United States Patent [19]

Korpman

[11] 4,024,312

[45] May 17, 1977

[54] PRESSURE-SENSITIVE ADHESIVE TAPE HAVING EXTENSIBLE AND ELASTIC BACKING COMPOSED OF A BLOCK COPOLYMER

[75] Inventor: Ralf Korpman, Bridgewater, N.J.

[73] Assignee: Johnson & Johnson, New Brunswick, N.J.

[22] Filed: June 23, 1976

[21] Appl. No.: 699,101

[52] U.S. Cl. .............................. 428/343; 128/156; 128/170; 428/909
[51] Int. Cl.² ...................... A61L 15/00; C09J 7/02
[58] Field of Search .................. 428/343, 355, 909; 128/156, 170

[56] References Cited

UNITED STATES PATENTS

| | | | |
|---|---|---|---|
| 2,349,710 | 5/1944 | Evans | 128/170 |
| 2,720,477 | 10/1955 | Lancaster | 428/343 |
| 2,734,503 | 2/1956 | Doyle | 128/156 |
| 2,823,728 | 2/1958 | Morgan | 156/249 |
| 2,862,846 | 12/1958 | Blackford et al. | 156/249 |
| 2,882,183 | 4/1959 | Bond et al. | 428/355 |
| 3,245,406 | 4/1966 | Chardack | 128/156 |
| 3,677,788 | 7/1972 | Zirnite | 128/170 |
| 3,684,644 | 8/1972 | Snell | 428/355 |
| 3,805,781 | 4/1974 | Hoeg | 128/156 |
| 3,876,454 | 4/1975 | Snell et al. | 428/355 |
| 3,885,559 | 5/1975 | Economow | 128/156 |
| 3,973,563 | 8/1976 | Green et al. | 428/343 |

OTHER PUBLICATIONS

Anon, Chemical Week, June 11, 1975, p. 35.

Primary Examiner—J.C. Cannon

[57] ABSTRACT

A highly conformable adhesive tape which comprises a highly extensible and elastic backing film laminated with an adhesive layer to form the tape. The adhesive is a normally tacky and pressure-sensitive elastomeric adhesive coated on at least one of the film surfaces. The film possesses a lengthwise elongation to break of at least about 200 percent, and a 50 percent rubber modulus of not above about 2,000 lbs./sq. inch. The tape is easily stretchable and normally may be removed easily from an application surface by stretching the tape lengthwise in a direction substantially parallel to the surface. This characteristic is highly important in medical applications where painless removal is desirable.

5 Claims, 4 Drawing Figures

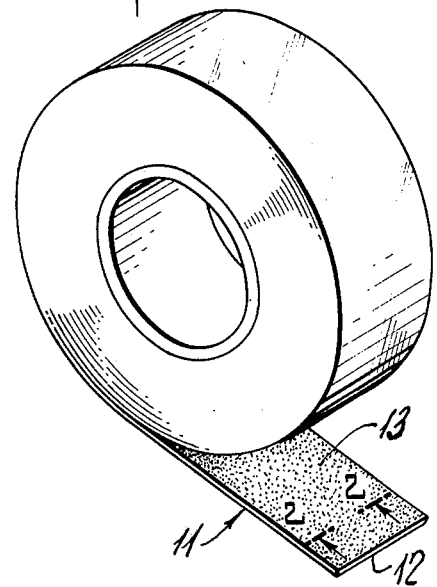
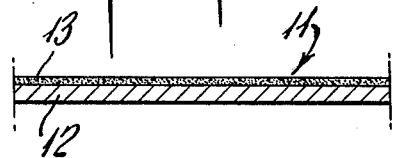
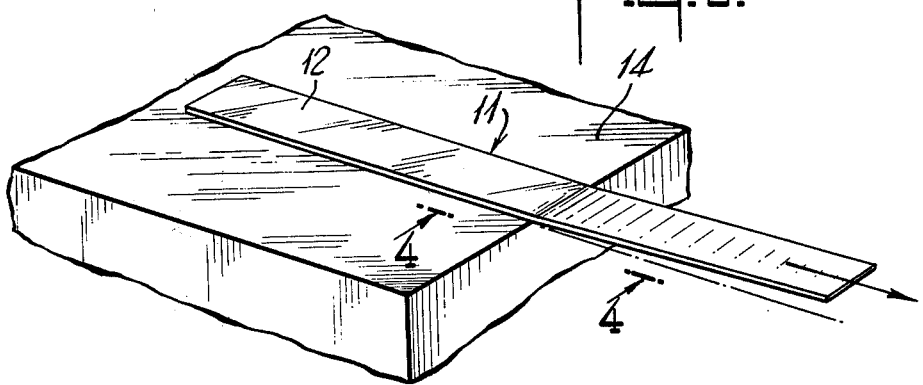
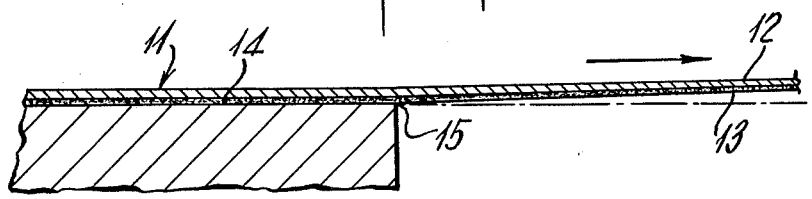

PRESSURE-SENSITIVE ADHESIVE TAPE HAVING EXTENSIBLE AND ELASTIC BACKING COMPOSED OF A BLOCK COPOLYMER

The present invention relates to normally tacky and pressure-sensitive adhesive tapes, more particularly to such tapes which comprise a highly elastomeric normally tacky and pressure-sensitive adhesive coated onto a basically nontacky backing film or sheet.

Prior art pressure-sensitive adhesive tapes of this type generally have had limited extensibility and elasticity due to the properties of the backing sheets employed. In fact, tapes made with paper, foil, or woven or nonwoven fabric backings have exhibited a low level of extensibility and virtually no elasticity although efforts have been made to incorporate extensibility by creping, or the like, and by impregnating papers and nonwovens with rubbery binders.

Plastic film-backed pressure-sensitive adhesive tapes have varied somewhat in properties depending upon the formulation and physical characteristics of the backing. Highly plasticized films, for instance, have had fairly high extensibility as compared with the unplasticized films. Both films however, have displayed a low order of elasticity.

I have invented a film backed normally tacky and pressure-sensitive adhesive tape which is highly extensible and highly elastic and which normally may be removed easily from an application surface by stretching it lengthwise in a direction substantially parallel to the plane of the surface.

The film backing of my tape is formed from a unique film forming composition comprising elastomeric and thermoplastic A-B-A block copolymers, and the film possesses a lengthwise elongation to break of at least about 200, preferably at least about 300, percent and a 50 percent rubber modulus of not above about 2,000 lbs./sq. inch. This low rubber modulus appears to be an important factor in insuring easy stretchability and easy removal of the tape at high elongations. In fact, in tapes used in absorbent dressings such as adhesive bandages, the thickness of the backing film is such that when one end of the tape is stretched lengthwise as described above, the tape and dressing are removed without pain from the skin. This "ouchless" removal appears to be a function of both the high extensibilty (elongation to break) and easy stretchability (low rubber modulus) of the film-adhesive laminate, as well as the thickness of the backing film and the laminate.

The elasticity of the backing film is important for conformability and other purposes. Preferably, the film possesses an elastic recovery from 50 percent stretch of at least about 75%, and more preferably at least about 90%. The backing film of this invention also is highly flexible and possesses a Gurley stiffness at a thickness of 1 mil of not above about one. A further advantage of the tape of this invention is that it remains flexible, extensible and elastic at very low temperatures and thus is highly advantageous for low temperature industrial applications.

The backing film of my invention is formed from an elastomeric and thermoplastic film forming composition which comprises an elastomeric component and 0–200 parts, preferably 85–200 parts of a resin component per one hundred parts by weight of the elastomeric component. The elastomeric component consists essentially of linear or radial A-B-A block copolymers wherein the A-blocks are thermoplastic and the B-blocks are elastomeric, or mixtures of these linear or radial A-B-A block copolymers with simple thermoplastic elastomeric A–B block copolymers. In these block copolymers the A-blocks are derived from styrene or sytrene homologues and the B-blocks are derived from conjugated dienes or lower alkenes. The proportion of A–B block copolymers in the mixture of A-B-A and A-B block copolymers should not exceed about 75 percent by weight and lower percentages normally would be used. The resin component consists essentially of low molecular weight resins, preferably having a number average molecular weight not above about 3,000, and which are adapted to associate principally with the thermoplastic A-blocks of the said block copolymers.

The A-B-A block copolymer of this invention are of the type which consist of A-blocks (end blocks) derived, i.e., polymerized, from styrene or styrene homologues; and B-blocks (center blocks) derived from conjugated dienes, such as isoprene or butadiene, or from lower alkenes, such as ethylene or butylene. Small proportions of other monomers also may enter into the block copolymer themselves. The individual A-blocks have a number average molecular weight of at least about 6,000, preferably in the range of about 8,000 – 30,000, and the A-blocks constitute about 5–50 percent, preferably about 10–30 percent, by weight of the block copolymer. The number average molecular weight of the B-blocks for linear A-B-A block copolymers preferably is in the range of about 45,000 – 180,000 and that of the linear copolymer, itself, preferably is in the range of about 75,000 – 200,000. The number average molecular weight of the radial A-B-A block copolymers preferably is in the range of about 125,000 – 400,000. The designation A-B-A includes what are sometimes called A-B-C block copolymers wherein the end blocks are different from one another but both are derived from styrene homologues. This applies both to linear and radial block copolymers. the term "linear block copolymer" (or copolymers) includes branched A-B-A copolymers as well as unbranched A-B-A copolymers.

The radial A-B-A polymers useful in this invention are of the type described in U.S. Pat. No. 3,281,383 and conform to the following general formula: $(A-B)_nX$, wherein A is a thermoplastic block polymerized from styrene or styrene homologues, B is an elastomeric block derived from conjugated dienes or lower alkenes, as indicated above, X is an organic or inorganic connecting molecule, with a functionality of 2–4 as described in U.S. Pat. No. 3,281,383 or possibly with a higher functionality as described in the article entitled "New Rubber is Backed by Stars" appearing on page 35 on the June 11, 1975 issue of *Chemical Week*. $n$ then is a number corresponding to the functionality of X.

The A-B block copolymers of this invention also are of the type wherein the A-blocks are derived from styrene or styrene homologues and the B-blocks are derived from conjugated dienes or polymers and copolymers derived from lower alkenes, either alone or in conjunction with small proportions of other monomers. The A-B block copolymers are described in U.S. Pat. Nos. 3,519,585 and 3,787,531.

The elastomeric component of the film forming composition of this invention may include small amounts of other more conventional elastomers but these should not exceed about 25 percent by weight of the elastomeric component. These other elastomers may include, highly broken down natural rubbers and butadiene-styrene random copolymer rubbers, synthetic polyisoprene, chloroprene rubbers, nitrile rubbers, butyl rubbers, and the like. Potentially elastomeric liquid polymers also may be employed as additives but normally in lower proportions not above about 10 percent by weight of the elastomeric component.

The resin component of the backing of this invention, if employed, consists essentially of low molecular weight resins which are adapted to associate principally with, and are principally compatible with, the thermoplastic A-blocks of the said block copolymers. These include low molecular weight resins based on poly-alpha-methylstyrene, polystyrene, polyvinyl toluene and similar aromatic resins, as well as copolymers thereof, coumarone indene and related cyclic compounds. Preferred resins for this purpose possess a number average molecular weight not above about 3,000 although higher molecular weight resins in the low molecular weight range also may be employed.

The film forming composition also may contain relatively small proportions of various other materials such as antioxidants, heat stabilizers and ultraviolet absorbers, release agents, extenders, fillers and the like. Typical antioxidants are 2,5 ditertiary amyl hydroquinone and ditertiary butyl cresol. Similarly, conventional heat stabilizers such as the zinc salts of alkyl dithiocarbamates may be used. Lecithin is one release material which has been found to be particularly suitable in minor amounts in this type of extrudable particulate mixture. However, waxes and various other release agents or slip agents may also be added in this manner. Relatively small proportions, in the neighborhood of 25 parts by weight of the elastomeric component, of various extenders such as higher molecular weight polystyrenes, nonreactive phenol-formaldehyde resins, linear polyester resins, polyethylene, polypropylene, etc., also may be included in the film forming composition of this invention. Similarly, the particulate mixture of this invention may include relatively small proportions, say 25 parts by weight of the elastomeric component, of fillers and pigments such as zinc oxide, aluminum hydrate, clay, calcium carbonate, titanium dioxide, carbon black and others. Many of these fillers and pigments also may be used in powdered form as parting agents to be mixed with thermoplastic elastomer particles to prevent these particles from agglomerating prior to blending with resin particles and other materials.

The normally tacky and pressure-sensitive adhesive of this invention may be a conventional elastomeric rubber-resin adhesive such as that disclosed in U.S. Pat. No. 2,909,278. However, the adhesive, like the backing film, also may be based upon an A-B-A block copolymer and therefore not only may be elastomeric but highly thermoplastic and extrudable. In this case the adhesive composition will include a tackifying resin which is adapted to associate principally with the elastomeric B-blocks of the block copolymer employed. Examples of such adhesives and tackifying resins are given in U.S. Pat. No. 3,676,202.

Other and further features and advantages of the adhesive tape of this invention will appear to one skilled in the art from the following description, examples and claims, taken together with the drawings wherein:

FIG. 1 is a view in perspective of a roll of pressure-sensitive adhesive tape according to one embodiment of this invention.

FIG. 2 is a partial sectional view along the line 2—2 of FIG. 1.

FIG. 3 is a view in perspective of the tape of this invention as the tape is stretched longitudinally for easy removal from an application surface.

FIG. 4 is an enlarged broken sectional view taken along the line 4 4 of FIG. 3.

Referring to FIGS. 1 and 2 of the drawings, there is shown a roll of normally tacky and pressure-sensitive adhesive tape 11 according to one embodiment of this invention which comprises a highly extensible and elastic backing film 12 and a pressure-sensitive adhesive layer 13 coated on one surface of the film. The opposite surface of the film 12 is coated with a release agent, not shown, to assure that the tape 11 will unwind readily after the tape is wound upon itself with the adhesive layer facing inwardly to form a tape roll, as shown in FIG. 1.

FIGS. 3 and 4 illustrate an important property of the tape of this invention, i.e., its easy removal from an application surface. When the tape 11 is applied to an application surface 14 as shown in FIGS. 3 and 4 with the adhesive layer 13 adhering to the surface, the tape of this invention may be removed easily from the surface by stretching the tape longitudinally by a force applied to its end. The high extensibility of the tape and its easy stretchability apparently cause the adhesive to release incrementally from the surface as the backing film begins to stretch substantially at the first point of contact with the surface. This first point of contact which can more properly be called the release point is shown at 15 in FIG. 4 and, of course, is a function of where the tape is adhered to the application surface. As this tape is stretched in the direction indicated by the arrow the adhesive will release from the application surface at point 15 and the release point will move along the tape away from the direction of pulling as the adhesive releases incrementally from the application surface.

While the simplest form of adhesive tape construction is shown in the drawings, it will be apparent to one skilled in the art that this invention embraces various other conventional pressure-sensitive adhesive tape constructions. For instance, for many applications, the tape may be marketed on a release liner such as a silicone coated paper. Diaper tapes, adhesive bandages, double-faced tapes, etc., normally use such silicone liners. The required release properties for the tape construction shown in the drawings may be obtained by incorporating a slip agent into the backing film itself, as well as by coating a release agent onto the film as described above.

The following examples of backing films, adhesives and adhesive tapes according to this invention are given only by way of illustration and are not intended to limit the scope of the invention in any way.

Table A gives the film compositions for six backing films of this invention, i.e. Examples I–VI, together with the physical characteristics of the films. In these examples, all proportions are expressed in parts per one hundred parts by weight of the total elastomeric component of the film unless otherwise indicated.

Film thickness is expressed in mils, or thousands of an inch, tensile strength in pounds per square inch to break the film as measured on an Instron tensile tester with an initial jaw separation of one inch at a speed of twelve inches per minute, and elongation is the percentage which the film must be stretched in a given direction to break it, i.e., stretched dimension at break minus normal dimension, over normal dimension in that direction, times a hundred. In all cases the designation "M.D." means "machine direction" lengthwise in the direction of processing and "C.D." means "cross direction."

Elastic recovery is percentage of immediate recovery in length after being stretched fifty (50) percent of original length and then released to allow free return. It is a function of the amount of stretch recovered over the amount of stretch. The amount of stretch equals the length when stretched minus the original length and the amount of stretch recovered equals the length when stretched minus the length after recovery. Rubber modulus is tensile stress in pounds per square inch of initial cross section measured at one half inch extension per inch of length of 50 percent elongation. This also is called 50 percent rubber modulus.

Gurley stiffness is measured as an opposite or inverse measure of flexibility with a standard Gurley stiffness tester using 1.0 by 1.5 inch samples with ¼ inch of sample in the jaw and ¼ inch overlapping the blade. The measured Gurley stiffness then is converted to stiffness at a thickness of one mil by dividing the measured stiffness by the cube of the measured thickness in mils.

Heat sealability is measured by clamping each film sample in an open sandwich with a sheet of standard fiberboard test material between the jaws of an Erich International Corporation Bag Sealer at 42 p.s.i. air pressure. The fiberboard is Standard Reference Material 1810 specified in United States Department of Commerce Standard for Tape Adhesion Testing No. 16 (M:L-B-131E, Class 2). One of the jaws is heated and the other is unheated. The boxboard is placed in contact with the heated jaw and the film in contact with the unheated jaw. Both jaws are cooled to ambient temperature by air jets prior to clamping. When the test material is in position between the jaws, the bottom jaw is heated by an electric heater to seal the film to the boxboard by heat transferred through the board. The heating time period required to heat the lower jaw to the minimum peak temperature necessary to permanently heat seal the film to the boxboard, using a clamping period of 4 seconds, then is measured. The minimum peak permanent heat sealing temperature corresponding to the time recorded, then is obtained by reference to a time-temperature calibration curve for the instrument obtained by measuring temperatures at the bonding surface of the boxboard. The minimum peak temperature referred to is that reached at the time the electric heater is deenergized at the end of the heating time period.

TABLE A

| Ingredients & Characteristics | I | II | III | IV | V | VI |
|---|---|---|---|---|---|---|
| Kraton 1107 S-I-S Linear Copolymer | 100 | 100 | 100 | | | 100 |
| Kraton 1102 S-B-S Linear Copolymer | | | | 100 | | |
| Solprene 420 S-I-S Radial Copolymer | | | | | 100 | |
| Amoco 18-290 Resin | | | 100 | | 100 | 125 |
| Piccotex 100 Resin | 100 | | | | | |
| Piccotex 120 Resin | | | | 100 | | |
| Cumar 509 LX Resin | | 125 | | | | |
| Zinc Dibutyl Dithiocarbamate (Antioxidant) | 1 | 1 | 1 | 1 | 2 | 1 |
| 2,5 Ditertiary Amyl Hydroquinone (Antioxidant) | ½ | ½ | ½ | ½ | ½ | ½ |
| Titanium Dioxide Pigment | | | 5 | | | |
| Thickness, (mils) | 3.3 | 4.5 | 3.6 | 8.5 | 4.2 | 3.2 |
| Rubber Modulus at 50% Elongation, lbs./in.$^2$ | 145 | 1925 | 800 | 450 | 115 | 1030 |
| Elongation (M.D.), % | 540 | 720 | 530 | 500 | 1200 | 330 |
| Elongation (C.D.), % | 760 | 1020 | 750 | 410 | 1140 | 720 |
| Tensile Strength (M.D.), lbs./in.$^2$ | 850 | 2480 | 1220 | 710 | 600 | 1340 |
| Tensile Strength (C.D.), lbs./in.$^2$ | 520 | 1840 | 1050 | 710 | 570 | 1090 |
| Gurley Stiffness, mg./in.$^2$/mil | 0.37 | 0.40 | 0.38 | 0.75 | 0.42 | 0.2 |
| Heat Sealing Temperature, ° F. | 150 | 250 | 250 | 280 | 240 | 270 |
| % Elastic Recovery After 50% Elongation | 82.5 | 92.5 | 98 | 78.5 | 95 | 92 |

It will be seen that the films of all of the above examples are quite elastic, i.e., possess an elastic recovery after 50 percent elongation of about 80 percent or more and generally well above 90 percent. In fact, all the films of the examples have an elastic recovery of over 90 percent except for those formulated with the Piccotex poly-alpha-methylstyrene-vinyl toluene resins. Furthermore, all the films possess a low rubber modulus, i.e., below about 2,000 lbs./in.$^2$ at 50 percent elongation and all but one have a modulus at 50 percent elongation of not above about 1,000 lbs./in.$^2$.

The films of the examples are not particularly oriented as evidenced from the tensile strength readings in the machine and cross-directions and generally possess a high elongation, i.e., at least about 500 percent in both directions. In fact, there are only two readings below 500 percent and these are well above 300 percent.

The films are highly flexible, exhibiting Gurley stiffness readings as low as 0.2 mg./in.$^2$/mil and no higher than 0.75 mg./in.$^2$/mil. The maximum permanent heat sealing temperature determined as described hereinbefore ranges between 150° F. and 280° F., well below 350° F.

Table B gives the compositions of three adhesives useful in the pressure-sensitive adhesive tapes of this invention. These are the compositions of Examples VII – IX. All proportions are expressed in parts per one hundred parts by weight of the total elastomers in the adhesive compositions.

TABLE B

| Ingredients | VII | VIII | IX |
|---|---|---|---|
| Kraton 1107 S-I-S Linear Copolymer | 100 | 40 | |
| Solprene 311X S-I Simple Copolymer | | 60 | |
| Raw Natural Rubber | | | 100 |
| Wingtack 95 Tackifier Resin | 80 | 60 | |
| Dehydrogenated Rosin Tackifier Resin | | | 85 |
| Particulate Silica | | | 10 |
| Lanolin | | | 25 |
| Titanium Dioxide | | | 60 |
| Zinc Dibutyl Dithiocarbamate | 2 | 2 | 2 |
| 2,5 Ditertiary Amyl Hydroquinone | 0.5 | 0.5 | 0.5 |

In Examples X – XV, normally tacky and pressure-sensitive adhesive tapes of this invention are produced first by coating one major surface of each of the films of Examples I – VI with the release agent of Example III of U.S. Pat. No. 3,502,497, then by applying selected adhesives of Examples VII – IX to the other major surface of the film, as described hereinafter. Due to the solvent sensitivity and elastic nature of the backing, special techniques should be used for coating and slitting the tape. A preferred method is to coat and dry, or extrude, the adhesive onto an nonelastic carrier such as a silicone coated release paper and laminate the film backing to the adhesive, preferably while the adhesive is still hot. The laminated tape with the carrier paper may be slit and used in this form either in strips or rolls or the tape may be rolled into log rolls without stretching as the liner is removed. Log rolls are normally slit on a lathe using an indexing knive which slits one roll at a time from the log roll to form tape rolls with the adhesive layer facing inwardly as shown in FIG. 1 of the drawings.

The following Table C shows the application of the adhesive compositions to the release coated backing films of these examples.

TABLE C

| Element | Examples | | | | | |
|---|---|---|---|---|---|---|
| | X | XI | XII | XIII | XIV | XV |
| Backing Films | I | II | III | IV | V | VI |
| Adhesive | VII | VII | VII | VII | VIII | IX |

In examples X– XII the adhesive is coated onto the backing from a solution of 50 percent solids in toluene and then dried to remove the toluene before slitting. In Examples XIII and XIV the adhesive is extruded hot onto a silicon coated paper release liner and then transferred to the backing film after cooling and before slitting. The adhesive of Example XV is coated from 30 percent solids in toluene, dried and slit as described hereinbefore. Each of the resulting normally tacky and pressure-sensitive adhesive tapes of Examples X – XV is highly conformable and flexible even at very low temperatures, and is highly extensible, easily stretchable and elastic as indicated hereinbefore. These tapes are removable easily from application surfaces merely by stretching them substantially in the direction of their length, and when applied to the human skin provide painless or "ouchless" removal in the same way.

In the foregoing examples Kraton 1107 copolymer is a thermoplastic elastomeric A-B-A (styrene-isoprene-styrene) block copolymer of this invention offered by the Shell Chemical Company, wherein the styrene content (that of the A-blocks) is about 12–15 percent, closer to 15 percent by weight of the block copolymer, and the polymer possesses a solution viscosity of about 2,000 centipoises at 25 percent solids in toluene at room temperature (using a Brookfield Viscometer with a No. 4 spindle at 60 r.p.m.), and a number average molecular weight of about 110,000 – 125,000. Kraton 1102 copolymer is another A-B-A block copolymer offered by Shell but this is a styrene-butadiene-styrene copolymer wherein the styrene blocks constitute about 30 percent of the copolymer. The number average molecular weight of Kraton 1102 copolymer also is about 125,000.

Solprene 420 copolymer is a radial styrene-isoprene-styrene block copolymer of the type described hereinbefore which has a number average molecular weight of 240,000 and a styrene content of about 15 percent. Solprene 311X is a simple A-B (styrene-isoprene) block copolymer having 15 percent sytrene. Both Solprenes are offered by Phillips Petroleum Company.

Cumar 509 LX resin is a solid coumarone indene resin offered by the Neville Chemical Company, and having a softening point of about 145° C. Amoco 18–290 resin is a solid poly-alpha-methylstyrene offered by Amoco Chemical Company, with a softening point of about 290° F. (143° C.). Piccotex 100 and 120 resins are poly-alpha-methylstyrene-vinyl toluene copolymers offered by Hercules Chemical Company, with melting points of 100° C. and 120° C., respectively.

Wingtack 95 tackifier resin is a solid tackifier resin consisting predominantly of polymerized structures derived from piperylene and isoprene, with the ratio of piperylene to isoprene derived structures being at least about 8 or 9 to 1, and with the remainder being derived from mono-olefins. It appears to contain about 12–15 percent unsaturation based upon percentage of units in each molecule having a double bond. The said resin is polymerized from a stream of aliphatic petroleum derivatives in the form of dienes and mono-olefins having 5 or 6 carbon atoms all in accordance with the general teachings of the aforeaid U.S. Pat. No. 3,577,398. This resin possesses a softening point of about 95° C. by the ball and ring method, a number average molecular weight of about 1,100 and is offered commercially by Goodyear Tire and Rubber Company.

Having now described the invention in specific detail and exemplified the manner in which it may be carried into practice, it will be readily apparent to those skilled in the art that innumerable variations, applications, modifications, and extensions of the basic principles involved may be made without departing from its spirit or scope.

What is claimed is:

1. A highly conformable adhesive tape which comprises a highly extensible and elastic backing film and a normally tacky and pressure-sensitive elastomeric adhesive layer on at least one pf the major surfaces of the film; and film being formed from an elastomeric and thermoplastic film forming composition which comprises an elastomeric component and 0–200 parts of a resin component per one hundred parts by weight of the elastomeric component, said elastomeric component consisting essentially of linear or radial A-B-A block copolymers or mixtures of these linear or radial A-B-A copolymers with simple A-B block copolymers, said A-blocks being derived from styrene or styrene homologues and said B-blocks being derived from conjugated dienes or lower alkenes, said resin component consisting essentially of low molecular weight resins adapted to associate principally with the thermoplastic A-blocks of said block copolymers; and said film possessing:
   a. a lengthwise elongation to break of at least about 200 percent,
   b. a rubber modulus of not above about 2,000 pounds per square inch, and
   c. an elastic recovery from 50 percent stretch of at least about 75 percent, whereby the tape normally may be removed easily by stretching it lengthwise to separate the adhesive from the application surface.

2. A highly conformable adhesive tape which comprises a highly extensible and elastic backing film and a normally tacky and pressure-sensitive elastomeric adhesive layer on at least one of the major surfaces of the film; said film being formed from an elastomeric and thermoplastic film forming composition which comprises an elastomeric component and 85–200 parts of a resin component per one hundred parts by weight of the elastomeric component, said elastomeric component consisting essentially of linear or radial A-B-A block copolymers or mixtures of these linear or radial A-B-A copolymers with simple A-B block copolymers, said A-blocks being derived from styrene or styrene homologues and said B-blocks being derived from conjugated dienes or lower alkenes, said resin component consisting essentially of low molecular weight resins adapted to associate principally with the thermoplastic A-blocks of said block copolymers; and said film possessing:

a. a lengthwise elongation to break of at least about 200 percent,
b. a rubber modulus of not above about 2,000 pounds per square inch, and
c. an elastic recovery from 50 percent stretch of at least about 75 percent, whereby the tape normally may be removed easily by stretching it lengthwise to separate the adhesive from the application surface.

3. An adhesive tape according to claim 1, wherein the film possesses an elastic recovery from 50 percent stretch of at least about 90 percent.

4. An adhesive tape according to claim 1, wherein the backing film possesses a Gurley stiffness at a thickness of 1 mil of not above about one.

5. An adhesive tape according to claim 1, wherein the proportion of the A-B block copolymers in the mixture of A-B-A and A-B block copolymers is not above about 75 percent by weight.

* * * * *

UNITED STATES PATENT AND TRADEMARK OFFICE
CERTIFICATE OF CORRECTION

PATENT NO. : 4,024,312
DATED : May 17, 1977
INVENTOR(S) : Ralf Korpman

It is certified that error appears in the above–identified patent and that said Letters Patent are hereby corrected as shown below:

In Column 4, line 10, "4 4" should read --- 4-4 ---.

In Column 5, line 39, "of 50" should read --- or 50 ---.

In Column 8, line 42, "pf" should read --- of ---.

Signed and Sealed this

Thirteenth Day of June 1978

[SEAL]

Attest:

RUTH C. MASON
Attesting Officer

DONALD W. BANNER
Commissioner of Patents and Trademarks